(12) United States Patent
Gordon

(10) Patent No.: US 11,850,303 B2
(45) Date of Patent: Dec. 26, 2023

(54) GEL AND A SUPPOSITORY AND METHODS TO PROVIDE THE GEL AND SUPPOSITORY

(71) Applicant: Uqora, Inc., San Diego, CA (US)

(72) Inventor: Spencer Gordon, San Diego, CA (US)

(73) Assignee: Uqora, Inc., San Diego, CA (US)

( * ) Notice: Subject to any disclaimer, the term of this patent is extended or adjusted under 35 U.S.C. 154(b) by 0 days.

(21) Appl. No.: 16/949,376

(22) Filed: Oct. 27, 2020

(65) Prior Publication Data

US 2022/0125717 A1    Apr. 28, 2022

(51) Int. Cl.
*A61K 9/06* (2006.01)
*A61K 9/02* (2006.01)
*A61K 31/191* (2006.01)
*A61K 31/7016* (2006.01)
*A61K 31/702* (2006.01)
*A61K 33/40* (2006.01)
*A61K 35/747* (2015.01)

(52) U.S. Cl.
CPC .............. *A61K 9/06* (2013.01); *A61K 9/02* (2013.01); *A61K 31/191* (2013.01); *A61K 31/702* (2013.01); *A61K 31/7016* (2013.01); *A61K 33/40* (2013.01); *A61K 35/747* (2013.01)

(58) Field of Classification Search
CPC ....................................................... A61K 9/06
See application file for complete search history.

(56) References Cited

U.S. PATENT DOCUMENTS

| 5,778,886 A * | 7/1998 | Shihata ................ A61K 9/0034 128/830 |
| 2016/0030306 A1 | 2/2016 | Martin et al. |
| 2016/0037504 A1 | 2/2016 | Tamura et al. |
| 2016/0031038 A1 | 10/2016 | Bergsma |
| 2017/0022474 A1 | 1/2017 | Palmerade Olvera et al. |
| 2017/0128396 A1 | 1/2017 | Guthrie |
| 2017/0224749 A1 | 8/2017 | Palmeira De Oliveira et al. |
| 2019/0142878 A1 | 5/2019 | Graf et al. |

FOREIGN PATENT DOCUMENTS

| EP | 1441769 B1 | 6/2005 |
| WO | 2009147173 A1 | 12/2009 |

OTHER PUBLICATIONS

Ingerdeientsnetwork.com (https://www.ingredientsnetwork.com/buffered-lactic-acid-prod668924.html#:~:text=Buffered%20lactic%20acid%20is%20a,with%20a%20desired%20ph%20value., accessed May 18, 2023) (Year: 2023).*
Uqora, Inc., Related Application, International PCT Application No. PCT/US2021/051130, International Search Report, dated Jan. 12, 2022.

(Continued)

*Primary Examiner* — Benjamin J Packard
(74) *Attorney, Agent, or Firm* — William Thomas Babbitt, Esq.

(57) ABSTRACT

A gel and suppository and method to provide the gel and the suppository, are disclosed herein. The gel comprising: between 50 and 150 millimolar of lactic acid concentrate; and between 0.5 and 10 millimolar of hydrogen peroxide concentrate. The suppository comprising: between 22.5 and 67.5 milligrams of lactic acid concentrate; and between 1 and 20 milligrams of hydrogen peroxide concentrate.

20 Claims, 6 Drawing Sheets

(56) References Cited

OTHER PUBLICATIONS

Uqora, Inc., Related Application, International PCT Application No. PCT/US2021/051130, Written Opinion of the Int'l Searching Authority, dated Jan. 12, 2022.

Uqora, Inc., Related Application, International PCT Application No. PCT/US2021/051130, Notice of the Transmittal of the Int'l Search Report and the Written Opinion of the Int'l Searching Authority, dated Jan. 12, 2022.

"Natural antimicrobials and their role in vaginal health: a short review." Dover, S.E et al., In. J. Probiotics Prebiotics, 2008, 3(4): 219-30.

"In vaginal fluid, bacteria associated with bacterial vaginosis can be suppressed with lactic acid but not hydrogen peroxide," O'Hanlon, et al., BMC Infectious Diseases 2011, 11:200.

\* cited by examiner

GEL AND A SUPPOSITORY AND METHODS TO PROVIDE THE GEL AND SUPPOSITORY

FIELD OF THE DISCLOSURE

The present disclosure relates to a gel, a liquid, and a suppository and methods to provide the gel and suppository.

BACKGROUND

The pH of a healthy vagina is acidic and ranges between 3.8 and 4.5. Rising vaginal pH is a sign of imbalance in the microbiome and leads to vaginal infections, primarily bacterial vaginosis (BV), trichomoniasis, candidiasis (yeast infection), and/or other infections. Vaginal pH may rise to 7 or above. Healthy vaginal microbiomes are dominated by lactobacillus bacteria that release lactic acid and hydrogen peroxide which lower pH and increase oxygen.

SUMMARY

One aspect of the present disclosure relates to a gel and a suppository that release comprise lactic acid and hydrogen peroxide. Such a combination of compounds may compensate for a lack of naturally released lactic acid and hydrogen peroxide to lower vaginal pH and improve the health of the vaginal microbiome. The gel may comprise of between 50 and 150 millimolar of lactic acid concentrate, between 0.5 and 10 millimolar of hydrogen peroxide concentrate, and/or other elements. The suppository may comprise of between 22.5 and 67.5 milligrams of lactic acid concentrate, between 1 and 20 milligrams of hydrogen peroxide concentrate, and/or other elements. By providing the gel and suppository, a consumer may facilitate balancing their vaginal pH level to prevent and/or treat infections and/or discomfort.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
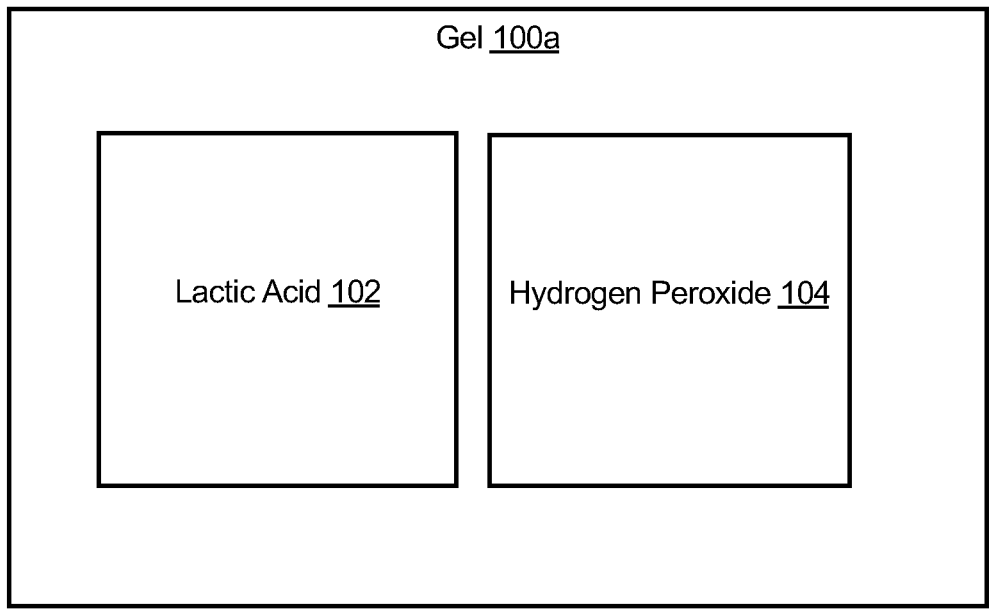
FIG. 1 illustrates a gel and a suppository, in accordance with one or more implementations.
Figure 1:
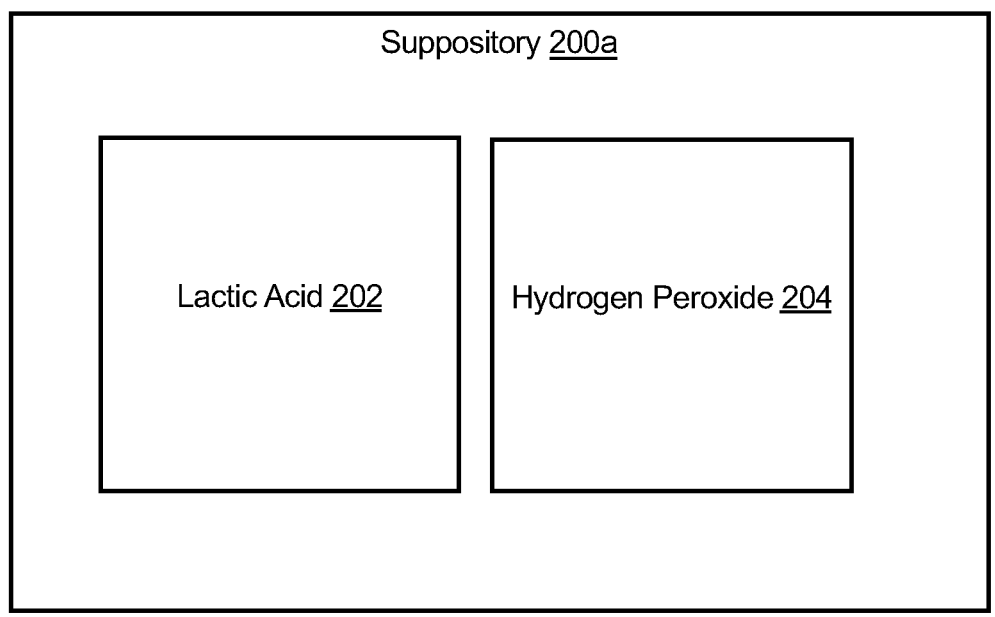

FIG. 1 illustrates a gel 100a and a suppository 200a, in accordance with one or more implementations. Gel 100a may comprise between 50 and 150 millimolar of lactic acid concentrate 102, between 0.5 and 10 millimolar of hydrogen peroxide concentrate 104, and/or other elements. The between 50 and 150 millimolar of lactic acid concentrate 102 may be combined with the between 0.5 and 10 millimolar of hydrogen peroxide concentrate 104 to comprise gel 100a.

In some implementations, gel 100a may comprise of between about 50 and 150 millimolar of lactic acid concentrate 102. In some implementations, the millimolar of lactic acid concentrate 102 in gel 100a may be greater than about 50 millimolar, 100 millimolar, 150 millimolar, may be less than about, and/or may be within a range bounded at the upper end by any concentration in the former listing of concentrations and bounded at the lower end by any concentration in the latter listing of concentrations.

In some implementations, gel 100a may comprise of about between 0.5 and 10 millimolar of hydrogen peroxide concentrate 104. In some implementations, the millimolar of hydrogen peroxide concentrate 104 in gel 100a may be greater than 0.5 millimolar, 5 millimolar, 10 millimolar, may be less than about, and/or may be within a range bounded at the upper end by any concentration in the former listing of concentrations and bounded at the lower end by any concentration in the latter listing of concentrations. In some implementations, gel 100a may be between 2 and 20 milliliters upon combining lactic acid concentrate 102 with hydrogen peroxide concentrate 104. In some implementations, gel 100a may be between about 2 and 20 milliliters upon combining lactic acid concentrate 102 with hydrogen peroxide concentrate 104.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±0.5 millimolar of the given numeric value provided such a deviation does not alter the end function or result of the value. Therefore, a value of about 2 millimolar can be construed to be a range from 1.5 millimolar to 2.5 millimolar. Furthermore, a range may be construed to include the start and the end of the range. For example, a range of 50 millimolar to 150 millimolar (i.e., range of 50-150 millimolar) includes 50 millimolar and also includes 150 millimolar, as well as millimolar in between 50 millimolar and 150 millimolar, unless explicitly stated otherwise herein.

Suppository 200a may comprise between 22.5 and 67.5 milligrams of lactic acid concentrate 202, between 1 and 20 milligrams of hydrogen peroxide concentrate 204, and/or other elements. The between 22.5 and 67.5 milligrams of lactic acid concentrate 202 may be combined with the between 1 and 20 milligrams of hydrogen peroxide concentrate 204 to comprise suppository 200a.

In some implementations, suppository 200a may comprise of between about 22.5 and 67.5 milligrams of lactic acid concentrate 202. In some implementations, the milligram of lactic acid concentrate 202 in suppository 200a may be greater than about 22.5 milligram, 35 milligram, 67.5 milligram, may be less than about, and/or may be within a range bounded at the upper end by any weight in the former listing of weights and bounded at the lower end by any weight in the latter listing of weights.

The term "about" can be construed as including a deviation of ±1 milligram of the given numeric value provided such a deviation does not alter the end function or result of the value. Therefore, a value of about 22.5 milligrams can be construed to be a range from 21.5 milligrams to 23.5 milligrams. Furthermore, a range may be construed to include the start and the end of the range. For example, a range of 22.5 milligrams to 67.5 milligrams (i.e., range of 22.5-67.5 milligrams) includes 22.5 milligrams and also includes 67.5 milligrams, as well as milligrams in between 22.5 milligrams and 67.5 milligrams, unless explicitly stated otherwise herein.

In some implementations, suppository 200a may comprise of about between 1 and 20 milligrams of hydrogen peroxide concentrate 204. In some implementations, the milligram of hydrogen peroxide concentrate 204 in suppository 200a may be greater than 1 milligram, 5 milligrams, 10 milligrams, 20 milligrams, may be less than about, and/or may be within a range bounded at the upper end by any weight in the former listing of weights and bounded at the lower end by any weight in the latter listing of weights. In some implementations, suppository 200a may be between 100 and 2,000 milligrams upon combining lactic acid concentrate 202 with hydrogen peroxide concentrate 204. In some implementations, suppository 200a may be between about 100 and 2,000 milligrams upon combining lactic acid concentrate 202 with hydrogen peroxide concentrate 204.

In some implementations, suppository 200a may further comprise of cocoa butter, polyethylene glycol, hydrogels, glycerinated gelatin, and/or other ingredients to encase lactic acid concentrate 202, hydrogen peroxide concentrate 204, and/or other elements. Thus, suppository 200a may be easily inserted into a body orifice of a consumer for delivery of lactic acid concentrate 202, hydrogen peroxide concentrate 204, and/or other elements to the consumer. In some implementations, suppository 200a may be inserted into the body orifice by utilizing an applicator.

Figure 2:
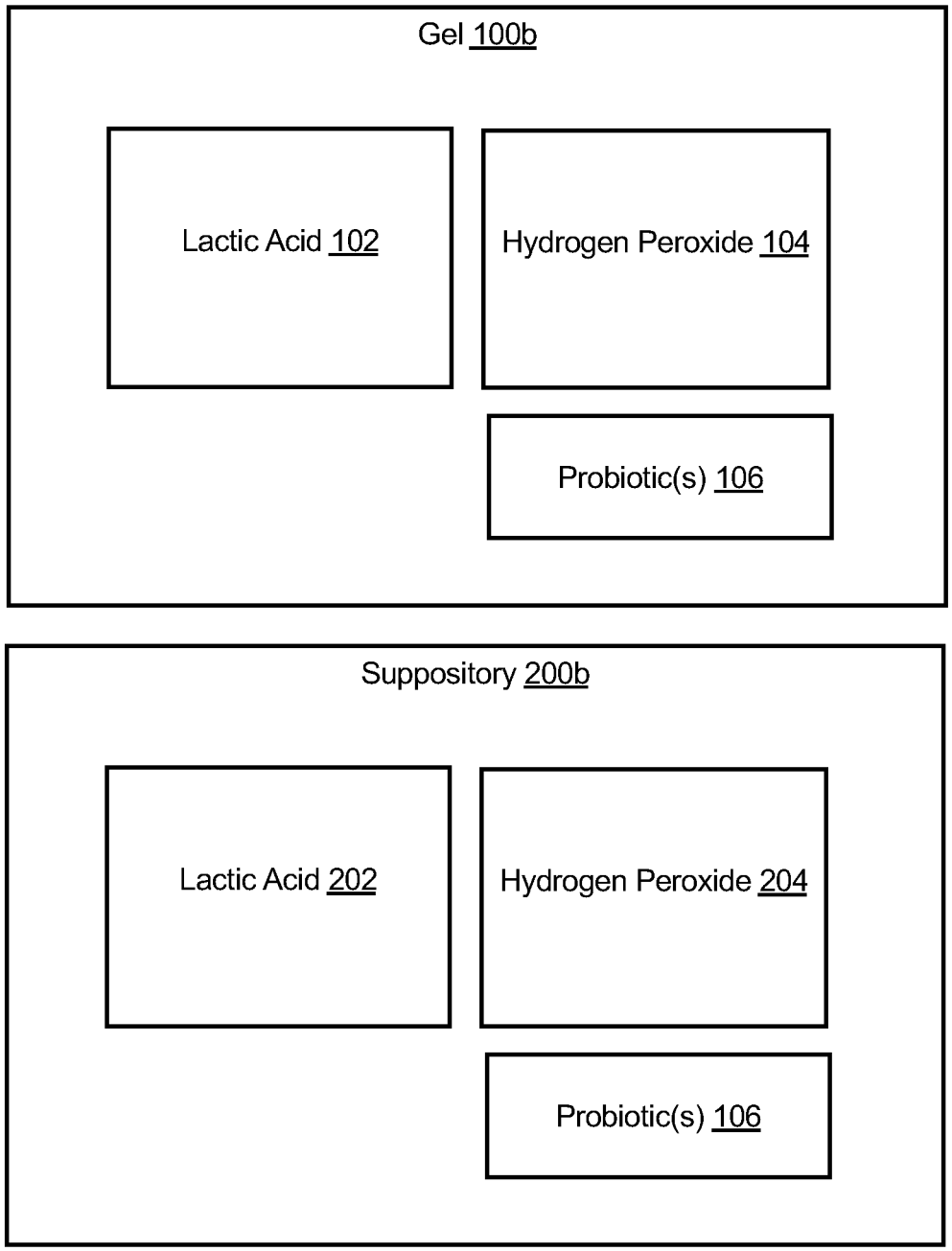
FIG. 2 illustrates the gel and the suppository, in accordance with one or more implementations.

FIG. 2 illustrates a gel 100b and a suppository 200b, in accordance with one or more implementations. Gel 100b may comprise of the between 50 and 150 millimolar of lactic acid concentrate 102, the between 0.5 and 10 millimolar of hydrogen peroxide concentrate 104, and/or other elements and the various implementations described thereof in FIG. 1 that may be combined, similar to gel 100a of FIG. 1. Suppository 200b may comprise of the between 22.5 and 67.5 milligrams of lactic acid concentrate 202, the between 1 and 20 milligrams of hydrogen peroxide concentrate 204, and/or other elements and the various implementations described thereof in FIG. 1 that may be combined, similar to suppository 200a of FIG. 1. Gel 100b and/or suppository 200b may further comprise probiotic(s) 106 other vitamins, and/or other elements. Probiotic(s) 106 may include lactobacilli and/or other probiotics.

In some implementations, gel 100b and/or suppository 200b may include between about 1 to 30 billion colony forming units (CFU) of probiotic(s) 106. In some implementations, the CFUs of probiotic(s) 106 in gel 100b and/or suppository 200b may be greater than about 1 billion CFU, 15 billion CFUs, 20 billion CFUs, 30 billion CFUs, may be less than about, and/or may be within a range bounded at the upper end by any number of bacteria in the former listing of numbers of bacteria and bounded at the lower end by any number of bacteria in the latter listing of number of bacteria.

Figure 3:
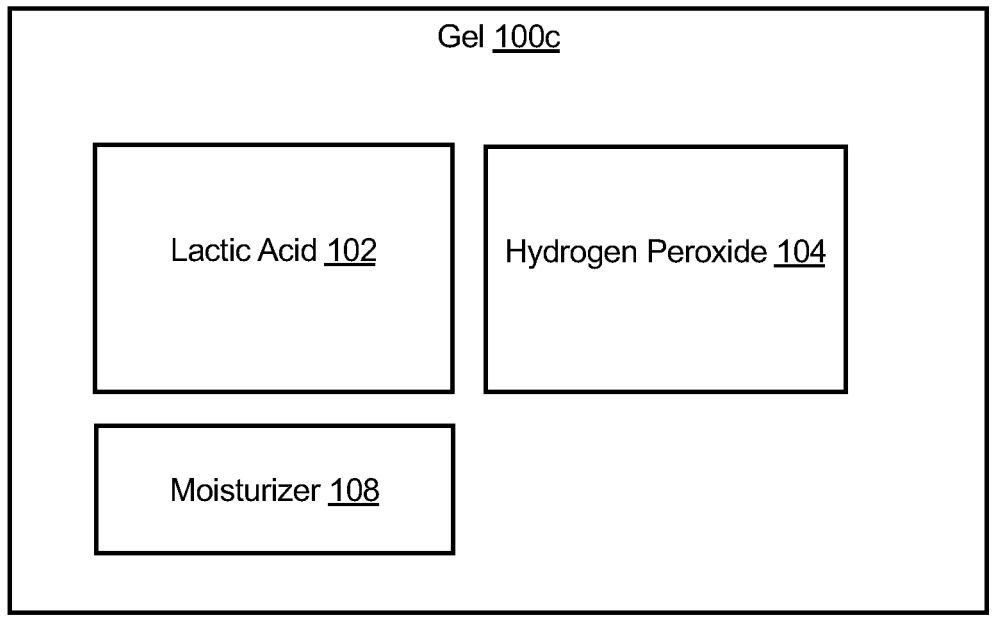
FIG. 3 illustrates the gel and the suppository, in accordance with one or more implementations.
Figure 3:
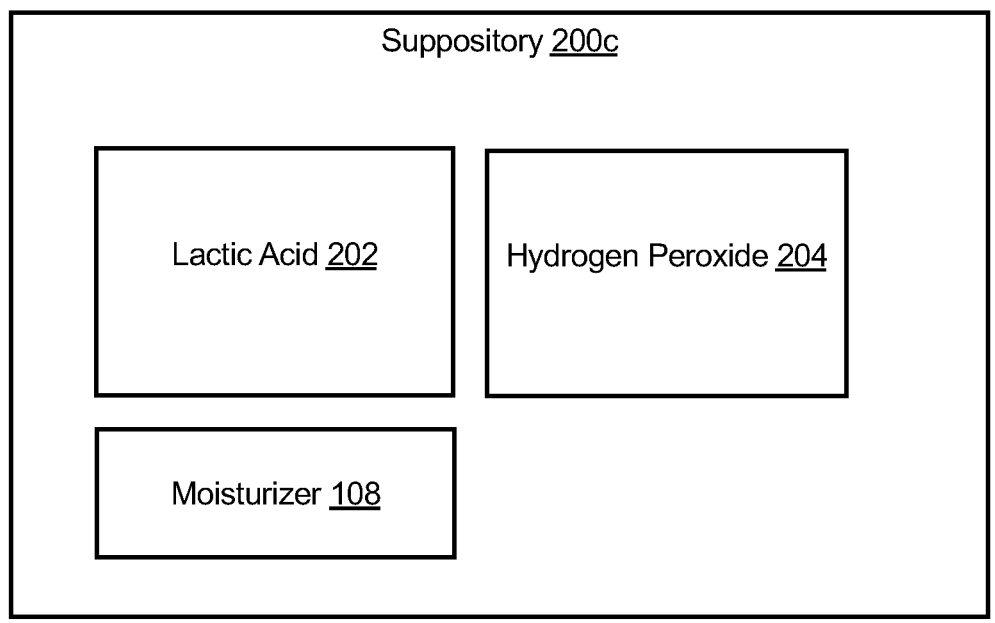

FIG. 3 illustrates a gel 100c and a suppository 200c, in accordance with one or more implementations. Gel 100c may comprise of the between 50 and 150 millimolar of lactic acid concentrate 102, the between 0.5 and 10 millimolar of hydrogen peroxide concentrate 104, and/or other elements and the various implementations described thereof in FIG. 1 that may be combined, similar to gel 100a of FIG. 1. Suppository 200c may comprise of the between 22.5 and 67.5 milligrams of lactic acid concentrate 202, the between 1 and 20 milligrams of hydrogen peroxide concentrate 204, and/or other elements and the various implementations described thereof in FIG. 1 that may be combined, similar to suppository 200a of FIG. 1. Gel 100c and/or suppository 200c may further comprise moisturizer 108 to facilitate and improve hydration and/or other elements. In some implementations, moisturizer 108 may be water-based or oil-based. In some implementations, moisturizer 108 may include glycerin, cocoa butter, aloe vera, and/or other moisturizers.

Figure 4:
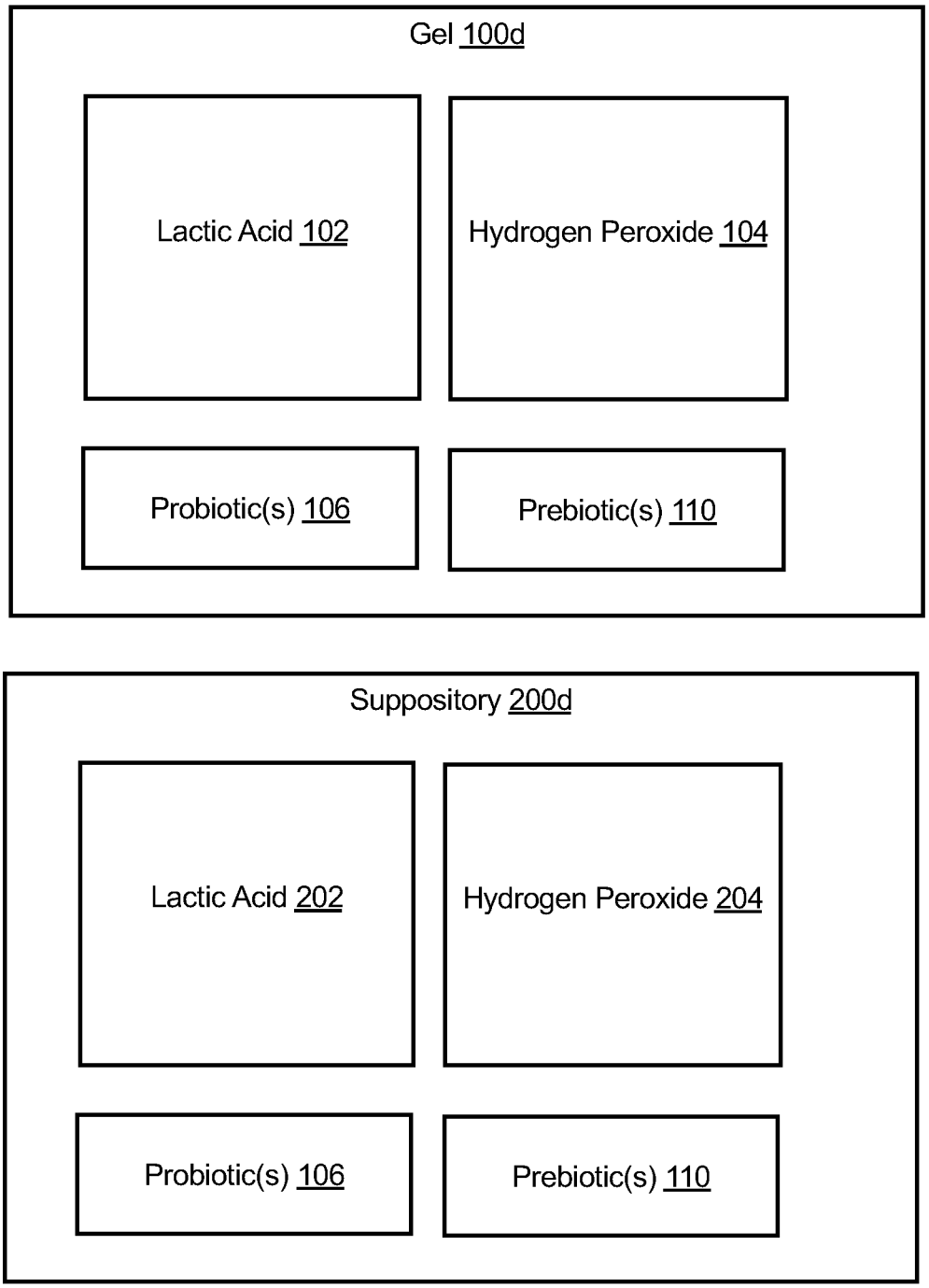
FIG. 4 illustrates the gel and the suppository, in accordance with one or more implementations.

FIG. 4 illustrates a gel 100d and a suppository 200d, in accordance with one or more implementations. Gel 100d may comprise of the between 50 and 150 millimolar of lactic acid concentrate 102, the between 0.5 and 10 millimolar of hydrogen peroxide concentrate 104, probiotic(s) 106, and/or other elements and the various implementations described thereof in FIG. 2 that may be combined, similar to gel 100b of FIG. 2. Suppository 200d may comprise of the between 22.5 and 67.5 milligrams of lactic acid concentrate 202, the between 1 and 20 milligrams of hydrogen peroxide concentrate 204, probiotic(s) 106, and/or other elements and the various implementations described thereof in FIG. 2 that may be combined, similar to suppository 200b of FIG. 2. Gel 100d and/or suppository 200d may further comprise prebiotic(s) 110 and/or other elements. Prebiotic(s) 110 may include lactose, oligofructose, and/or other prebiotics.

In some implementations, gel 100d and/or suppository 200d may include between about 10 to 100 milligrams of prebiotic(s) 110. In some implementations, the milligram of prebiotic(s) 110 in gel 100d and/or suppository 200d may be greater than about 10 milligrams, 25 milligrams, 50 milligrams, 100 milligrams, may be less than about, and/or may be within a range bounded at the upper end by any weight in the former listing of weights and bounded at the lower end by any weight in the latter listing of weights.

Figure 5:
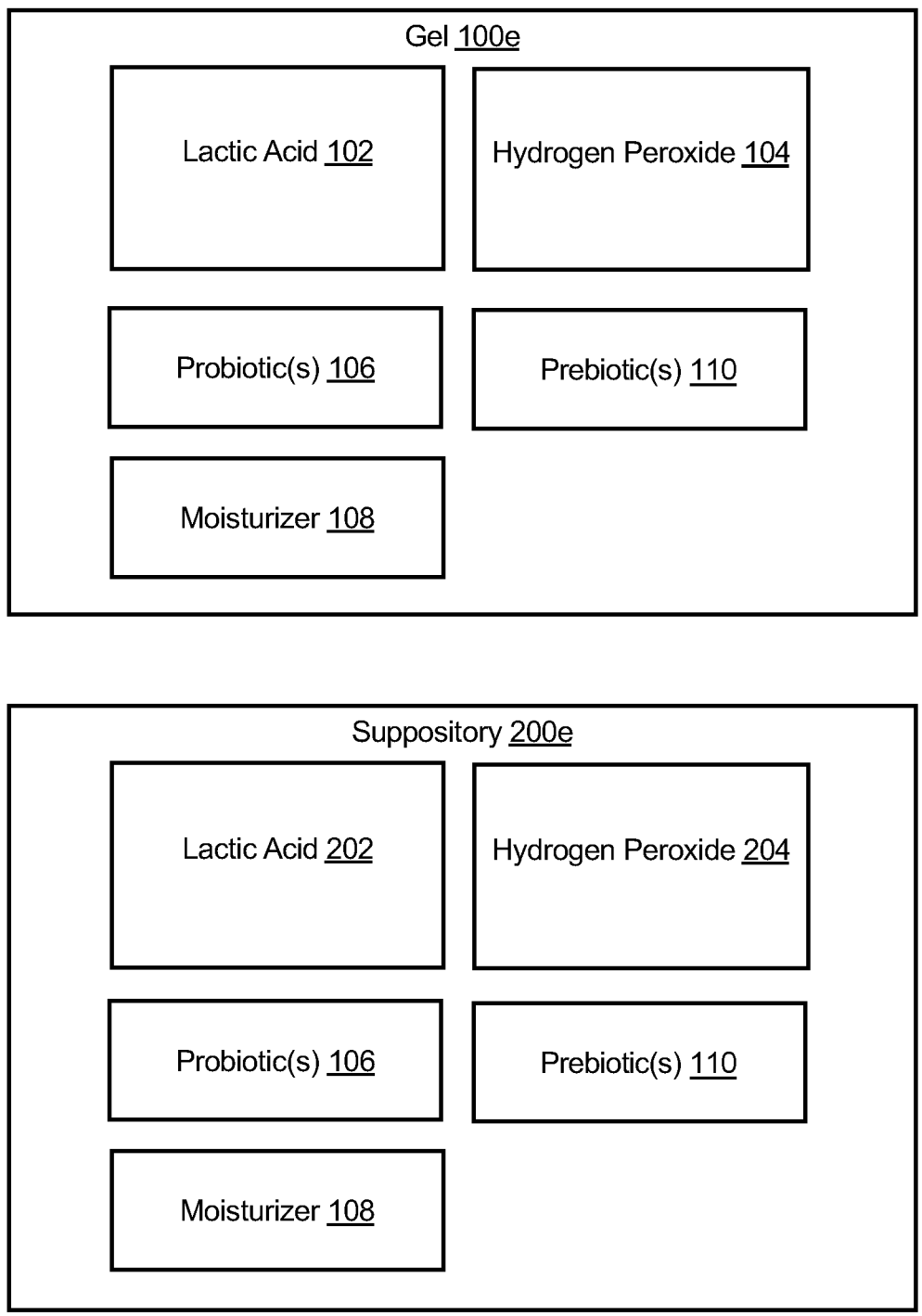
FIG. 5 illustrates the gel and the suppository, in accordance with one or more implementations.

FIG. 5 illustrates a gel 100e and a suppository 200e, in accordance with one or more implementations. Gel 100e may comprise of the between 50 and 150 millimolar of lactic acid concentrate 102, the between 0.5 and 10 millimolar of hydrogen peroxide concentrate 104, probiotic(s) 106, prebiotic(s) 110 and/or other elements and the various implementations described thereof in FIG. 4 that may be combined (similar to gel 100d of FIG. 4) in addition to moisturizer 108 as described in FIG. 3. Suppository 200e may comprise of the between 22.5 and 67.5 milligrams of lactic acid concentrate 202, the between 1 and 20 milligrams of hydrogen peroxide concentrate 204, probiotic(s) 106, prebiotic(s) 110 and/or other elements and the various implementations described thereof in FIG. 4 that may be combined (similar to suppository 200d of FIG. 4) in addition to moisturizer 108 as described in FIG. 3.

In some implementations, the lactic acid concentrate 102, the hydrogen peroxide concentrate 104, and/or other elements comprising gel 100a-e of FIG. 1-5, and various implementations of concentrations described herein, may comprise a liquid rinse solution (not pictured). The liquid rinse solution may enable the consumer to stream, and thus apply, the lactic acid concentrate 102, the hydrogen peroxide concentrate 104, and/or other elements into their body via one or more of a liquid storage unit, a pressure pump, a tube, a nozzle, and/or other components.

Figure 6:
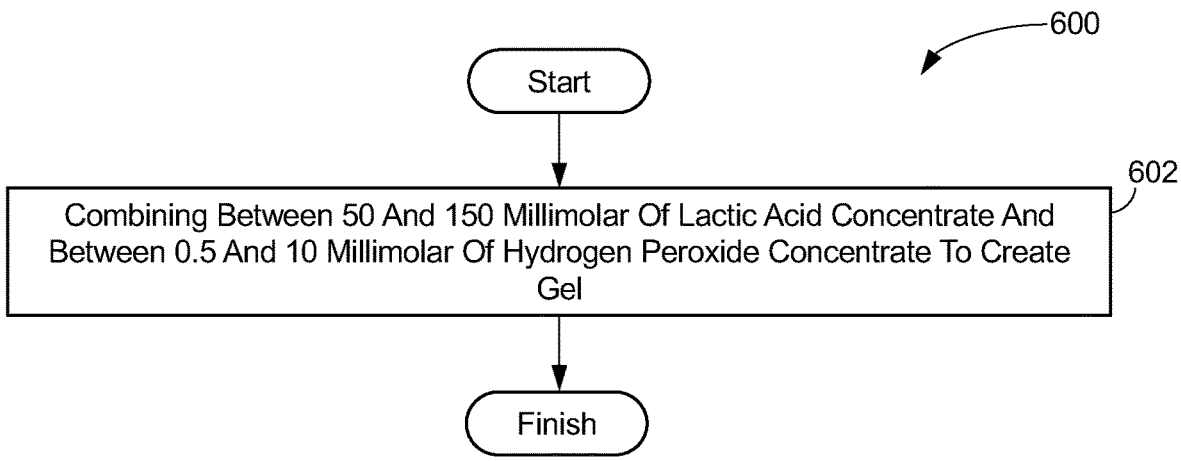
FIG. 6 illustrates a method to provide a gel, in accordance with one or more implementations.

FIG. 6 illustrates a method 600 to provide a gel, in accordance with one or more implementations. The operations of method 600 presented below are intended to be illustrative. In some implementations, method 600 may be accomplished with one or more additional operations not described, and/or without one or more of the operations discussed. Additionally, the order in which the operations of method 600 are illustrated in FIG. 6 and described below is not intended to be limiting.

An operation 602 may include combining between 50 and 150 millimolar of lactic acid concentrate and between 0.5 and 10 millimolar of hydrogen peroxide concentrate to create the gel.

Figure 7:
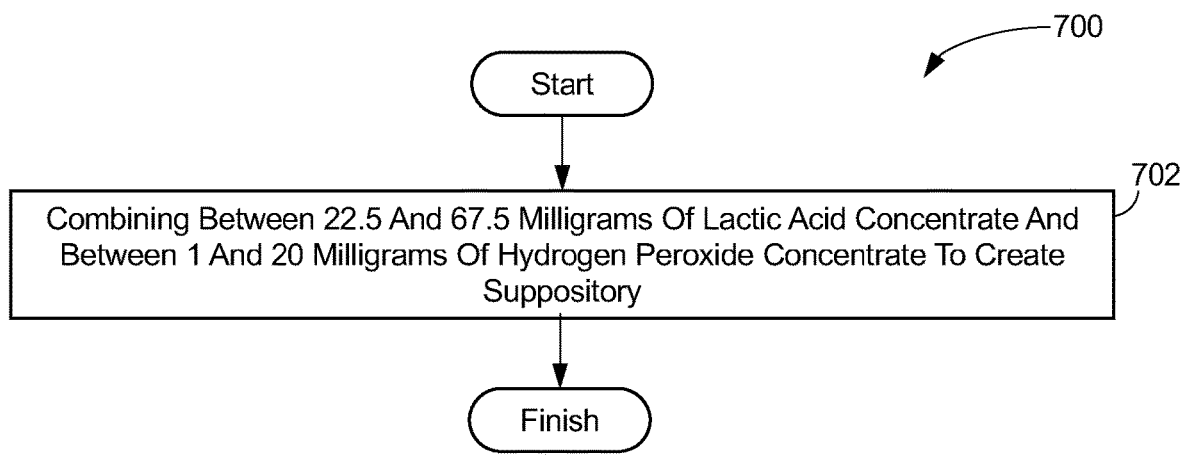
FIG. 7 illustrates a method to provide a suppository, in accordance with one or more implementations.

FIG. 7 illustrates a method 700 to provide a suppository, in accordance with one or more implementations. The operations of method 700 presented below are intended to be illustrative. In some implementations, method 700 may be accomplished with one or more additional operations not described, and/or without one or more of the operations discussed. Additionally, the order in which the operations of method 700 are illustrated in FIG. 7 and described below is not intended to be limiting.

An operation 702 may include combining between 22.5 and 67.5 milligrams of lactic acid concentrate and between 1 and 20 milligrams of hydrogen peroxide concentrate to create the suppository.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A gel, the gel consisting of:
   between 50 and 150 millimolar of lactic acid concentrate;
   between 0.5 and 10 millimolar of hydrogen peroxide concentrate, wherein the between 50 and 150 millimolar of lactic acid concentrate is combined with the between 0.5 and 10 millimolar of hydrogen peroxide concentrates; and
   optionally, at least one of a probiotic, a prebiotic, a vitamin and a moisturizer.

2. The gel of claim 1, wherein the gel is between 2 and 20 milliliters.

3. The gel of claim 1 wherein the gel comprises:
   between 1 to 30 billion colony forming units of a probiotic; and/or between 10 and 100 milligrams of a prebiotic.

4. The gel of claim 1, wherein:
   the probiotic, if present, comprises a lactobacilli, and
   the prebiotic, if present, comprises lactose and/or oligofructose.

5. The gel of claim 1 wherein the gel comprises a moisturizer.

6. A suppository, the suppository consisting of:
   between 22.5 and 67.5 milligrams of lactic acid concentrate;
   between 1 and 20 milligrams of hydrogen peroxide concentrate, wherein the between 22.5 and 67.5 milligrams of lactic acid concentrate is combined with the between 1 and 20 milligrams of hydrogen peroxide concentrate; and
   optionally, at least one of a probiotic, a prebiotic, a moisturizer, a vitamin, a polyethylene glycol, a hydrogel, and a glycerinated gelatin.

7. The suppository of claim 6, wherein the suppository is between 100 and 2,000 milligrams.

8. The suppository of claim 6 wherein the suppository comprises:
   between 1 to 30 billion colony forming units of a probiotic, and/or between 10 and 100 milligrams of a prebiotic.

9. The suppository of claim 8, wherein:
   the probiotic, if present, comprises a lactobacilli, and
   the prebiotic, if present comprises lactose and/or oligofructose.

10. The suppository of claim 6 wherein the suppository comprises a moisturizer.

11. A method to provide a gel, the method comprising:
    forming a gel consisting of a combination of between 50 and 150 millimolar of lactic acid concentrate and between 0.5 and 10 millimolar of hydrogen peroxide concentrate and, optionally, at least one of a probiotic, a prebiotic, a vitamin and a moisturizer.

12. The method of claim 11, wherein the formed gel is between 2 and 20 milliliters.

13. The method of claim 11 wherein the gel comprises a probiotic in an amount of between 1 to 30 billion colony forming units and a prebiotic in an amount of between 10 and 100 milligrams.

14. The method of claim 13, wherein:
    the probiotic comprises lactobacilli, and
    the prebiotic comprises lactose and/or oligofructose.

15. The method of claim 11 wherein the gel comprises a moisturizer.

16. A method to provide a suppository, the method comprising:
    forming a suppository consisting of a combination of between 22.5 and 67.5 milligrams of lactic acid concentrate and between 1 and 20 milligrams of hydrogen peroxide concentrate and, optionally, at least one of a probiotic, a prebiotic, a moisturizer, a vitamin, a polyethylene glycol, a hydrogel, and a glycerinated gelatin.

17. The method of claim 16, wherein the suppository is between 100 and 2,000 milligrams.

18. The method of claim 16 wherein the suppository comprises a probiotic in an amount of between 1 to 30 billion colony forming units; and a prebiotic in an amount of between 10 and 100 milligrams.

19. The method of claim 18, wherein:
    the probiotic comprises a lactobacilli, and
    the prebiotic comprises lactose and/or oligofructose.

20. The method of claim 16 wherein the suppository comprises a moisturizer.

* * * * *